United States Patent
Shi et al.

(10) Patent No.: US 11,203,523 B2
(45) Date of Patent: Dec. 21, 2021

(54) BIONIC SERS SUBSTRATE WITH METAL-BASED COMPOUND EYE BOWL STRUCTURE AND ITS CONSTRUCTION METHOD AND APPLICATION

(71) Applicant: JIANGNAN UNIVERSITY, Wuxi (CN)

(72) Inventors: Gang Shi, Wuxi (CN); Ying Li, Wuxi (CN); Jianhua Li, Wuxi (CN); Xuan Jin, Wuxi (CN); Dawei Wang, Wuxi (CN); Likui Wang, Wuxi (CN); Jingguo Yang, Wuxi (CN); Xinxin Sang, Wuxi (CN); Caihua Ni, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 17/082,878

(22) Filed: Oct. 28, 2020

(65) Prior Publication Data
US 2021/0114868 A1    Apr. 22, 2021

(30) Foreign Application Priority Data

Oct. 29, 2019    (CN) .......................... 201911038168.0

(51) Int. Cl.
*B81B 7/04* (2006.01)
*B81C 1/00* (2006.01)
(Continued)

(52) U.S. Cl.
CPC ............ *B81B 7/04* (2013.01); *B81C 1/00214* (2013.01); *B81C 99/0085* (2013.01);
(Continued)

(58) Field of Classification Search
CPC ............................. B81C 1/00373; B81B 7/04
See application file for complete search history.

(56) References Cited

FOREIGN PATENT DOCUMENTS

| CN | 102674236 A | 9/2012 |
|---|---|---|
| CN | 108996469 A | 12/2018 |

OTHER PUBLICATIONS

Lee et al 3D plasmonic nanobowl platform for the study of exosomes in solution.*

(Continued)

*Primary Examiner* — Moazzam Hossain
(74) *Attorney, Agent, or Firm* — CBM Patent Consulting, LLC

(57) ABSTRACT

The present invention discloses a bionic SERS substrate of a metal-based compound eye bowl structure, a construction method and application. The bionic SERS substrate of the metal-based compound eye bowl structure of the present invention consists of a metal bowl and a cone-shaped structure substrate in an ordered hierarchy manner. The metal bowl is of a continuously and closely arranged single-layer bowl structure. A height of the metal bowl is 0.01-10 μm, and a bowl opening diameter is 0.01-10 μm. A cone is a micron pyramid cone, and a height of the micron pyramid cone is 1-100 μm. The present invention assembles the metal bowl on a surface of the substrate of the micron pyramid cone structure with great fluctuation by a solid-liquid interface chemical reduction method and a small ball template method, and further constructs a 3D SERS substrate with a bionic compound eye structure.

4 Claims, 4 Drawing Sheets

(51) Int. Cl.
  B81C 99/00 (2010.01)
  B82Y 30/00 (2011.01)
  B82Y 40/00 (2011.01)
  C23C 18/16 (2006.01)
  C23C 18/38 (2006.01)
  C23C 18/42 (2006.01)
  G01N 21/65 (2006.01)
  G01N 33/02 (2006.01)

(52) U.S. Cl.
  CPC ............... B82Y 30/00 (2013.01); B82Y 40/00 (2013.01); C23C 18/1646 (2013.01); C23C 18/1657 (2013.01); C23C 18/38 (2013.01); C23C 18/42 (2013.01); G01N 21/658 (2013.01); *B81B 2201/02* (2013.01); *B81B 2203/0384* (2013.01); *G01N 33/025* (2013.01)

(56) References Cited

OTHER PUBLICATIONS

Das et al Large-Scale Plasmonic nanoCones Array For Spectroscopy Detection.*

Li Yang, et al. "Functional two-dimensional ordered array study progress based on single-layer colloidal crystals", Li Yang, et al., Chinese Science Bulletin, Sep. 13, 2016 vol. 62, No. 6, pp. 508-518.

* cited by examiner

BIONIC SERS SUBSTRATE WITH METAL-BASED COMPOUND EYE BOWL STRUCTURE AND ITS CONSTRUCTION METHOD AND APPLICATION

This application claims priority to Chinese Patent Application Ser. No. CN201911038168.0 filed on 29 Oct. 2019.

TECHNICAL FIELD

The present invention relates to a bionic SERS substrate of a metal-based compound eye bowl structure, a construction method and application, and belongs to the technical fields of nano materials and nanochemistry.

BACKGROUND ART

A composite material with a specific structure is designed by compounding single nano materials, so that the composite material has intrinsic performance, and is also endowed with new special functions. By regulating and controlling the material in this mode, the performance limitation of a single-component material is broken through, and excellent application prospects are realized in the aspects of development of functional new materials, effective utilization of energy, pollution treatment and function detection. A bionic nano structure plays an important role in preparing nano composite materials, such as trace sensors, flat panel displays, self-cleaning color-changing glass and solar cells. These bionic micro-nano structures can effectively improve the mechanical, optical and electrical performance.

In 1974, Fleischmann, et al. obtained a high-quality pyridine Raman spectrum, known as Surface Enhanced Raman Spectrum (SERS), by performing roughening treatment on the smooth surface of a silver electrode. SERS can provide abundant structural information at the molecular level, and can effectively overcome the limitation of low sensitivity and susceptibility to interference from other molecules in a detection solution of the conventional Raman technique, so that high-intensity Raman signals of detection molecules can be easily detected, and the sensitivity is very high. On some well-designed metal (such as Au and Ag) nanostructures, the ultra-high sensitivity even at a single molecule level can be achieved.

A metal bowl is a patterned array for effectively enhancing the Raman signal, can effectively enhance the electromagnetic field intensity on the surface of the structure noble metal, has more "hot spots", and shows strong optical characteristics, so that the metal bowl is widely studied in SERS. For example, Yang, et al. prepared an SERS nanobowl array with an adjustable surface nanostructure by the template limitation dehumidification technology, and high sensitivity and the near infrared range of the laser wavelength could be realized. Rao, et al. manufactured a 2D Au nanobowl array with an enhancing factor capable of reaching $1.27 \times 10^7$ by the chemical adsorption and inversion technology. Wang, et al. prepared embedded silver nanobowl plasma crystals by the soft nanoimprint and electronic beam evaporation technology, and the embedded silver nanobowl plasma crystals were used for fast detection of polychlorinated biphenyl (PCB-77). Li, et al. manufactured an Au—Ag composite SERS nanobowl array through polystyrene ball self assembly (PS) and atom layer deposition (ALD), and the Au—Ag composite SERS nanobowl array could be used as a functional assembly in high-sensitivity spectroscopy and biosensors. However, the metal bowl has poor structural stability, is very easy to damage when being transferred to a three-dimensional substrate with great fluctuation, and the metal bowl array with a solid bottom cannot be induced to be assembled on the surface of the three-dimensional substrate with great fluctuation.

SUMMARY OF THE INVENTION

In order to solve the technical problem, the present invention assembles a metal bowl on a surface of a substrate of a micron pyramid cone structure with great fluctuation by a solid-liquid interface chemical reduction method and a small ball template method, and further constructs a 3D SERS substrate with a bionic compound eye structure. The bionic SERS substrate has more electromagnetic field enhanced "hot spots", and can improve the utilization efficiency on incident laser at the same time. When being applied to detection on harmful substances in water resources and food, the bionic SERS substrate has the advantages of high sensitivity, excellent linearity, strong anti-interference performance, good repeatability and the like, and has huge potentials in the aspect of safety monitoring.

A first objective of the present invention is to provide a composite substrate. The composite substrate includes a cone-shaped structure substrate and a nano material coating a surface of the cone-shaped structure substrate. The nano material is a nanobowl-shaped material or a hollow nanoneedle-shaped material. The cone-shaped structure substrate has a height of 0.1-100 μm. The nanobowl has a height of 0.01-10 μm and a bowl opening diameter of 0.01-10 μm. A hollow nanoneedle has a length of 0.1-10 μm, a wall thickness of 5-100 nm, an upper narrow opening diameter of 5-1,000 nm, and a lower narrow opening diameter of 10-1,100 nm.

Further, the nanobowl-shaped material is one or two of a semiconductor or a metal.

Further, the hollow nanoneedle-shaped material is one or two of a semiconductor or a metal.

Further, the semiconductor is one or a compound of more of silicon, metal oxide, metal sulfide, metal phosphide or a conductive polymer.

Further, the metal is one or more of gold, silver, palladium, platinum, copper, lithium or sodium.

Further, the nanobowl-shaped material is a semiconductor bowl, and the surface of the semiconductor bowl is modified with metal particles.

Further, the cone-shaped structure substrate is a regular cone or an irregular cone.

A second objective of the present invention is to provide a bionic SERS substrate of a metal-based compound eye bowl structure. The bionic SERS substrate of the metal-based compound eye bowl structure includes a cone-shaped structure substrate and a metal bowl coating a surface of the cone-shaped structure substrate. The metal bowl is of a continuously and closely arranged single-layer bowl structure. The metal bowl has a height of 0.01-10 μm, and a bowl opening diameter of 0.01-10 μm. The cone is a micron pyramid cone, and the micron pyramid cone has a height of 1-100 μm.

Further, a material of the metal bowl is one or more of gold, silver, palladium, platinum, copper, lithium or sodium.

Further, a material of the cone-shaped structure substrate is one or more of silicon, silicon dioxide, metal oxide, metal sulfide, metal phosphide, a thermosetting polymer, a thermoplastic polymer, a photocuring polymer, polydimethylsiloxane or a derivative of these materials.

A third objective of the present invention is to provide a construction method of the bionic SERS substrate of the metal-based compound eye bowl structure. The construction method includes the following steps:

(1) performing self-assembly on small balls with a diameter of 0.01-10 μm in a gas-liquid interface to obtain closely arranged single-layer balls;

(2) transferring the single-layer balls obtained in step (1) to a gas-liquid interface of a precursor reaction solution required for preparing a metal bowl to grow metal films on surfaces of the small balls below the liquid level in situ, so as to obtain the small balls with the metal films attached to the lower surfaces; and (3) transferring the small balls with the metal films attached to the lower surfaces obtained in step (2) to the surface of the cone-shaped structure substrate, and then removing the small balls to obtain the bionic SERS substrate of the metal-based compound eye bowl structure.

Further, the precursor reaction solution required for preparing the metal bowl is a reaction solution containing one or more elements of gold, silver, palladium, platinum, copper, lithium or sodium.

Further, a material of the small balls is one of silicon dioxide, polystyrene, polymethyl methacrylate, polyacrylic acid, polylactic acid, chitosan, gelatin, albumin, starch or a derivative of these materials.

Further, in step (3), during transferring, the cone-shaped structure substrate is used for directly supporting the small balls with the metal films attached to the lower surfaces from a solution.

A fourth objective of the present invention is to provide application of the bionic SERS substrate of the metal-based compound eye bowl structure to the field of Raman sensing.

Further, the application includes detection on harmful substances in water resources and food.

The present invention has the following beneficial effects:

The present invention assembles the metal bowl on a surface of the substrate of the micron pyramid cone structure with great fluctuation by a solid-liquid interface chemical reduction method and a small ball template method, and further constructs a 3D SERS substrate with a bionic compound eye structure. The bionic SERS substrate has more electromagnetic field enhanced "hot spots", and can improve the utilization efficiency on incident laser at the same time. When being applied to detection on harmful substances in water resources and food, the bionic SERS substrate has the advantages of high sensitivity, excellent linearity, strong anti-interference performance, good repeatability and the like, and has huge potentials in the aspect of safety monitoring.

DETAILED DESCRIPTION OF THE INVENTION

Figure 1:
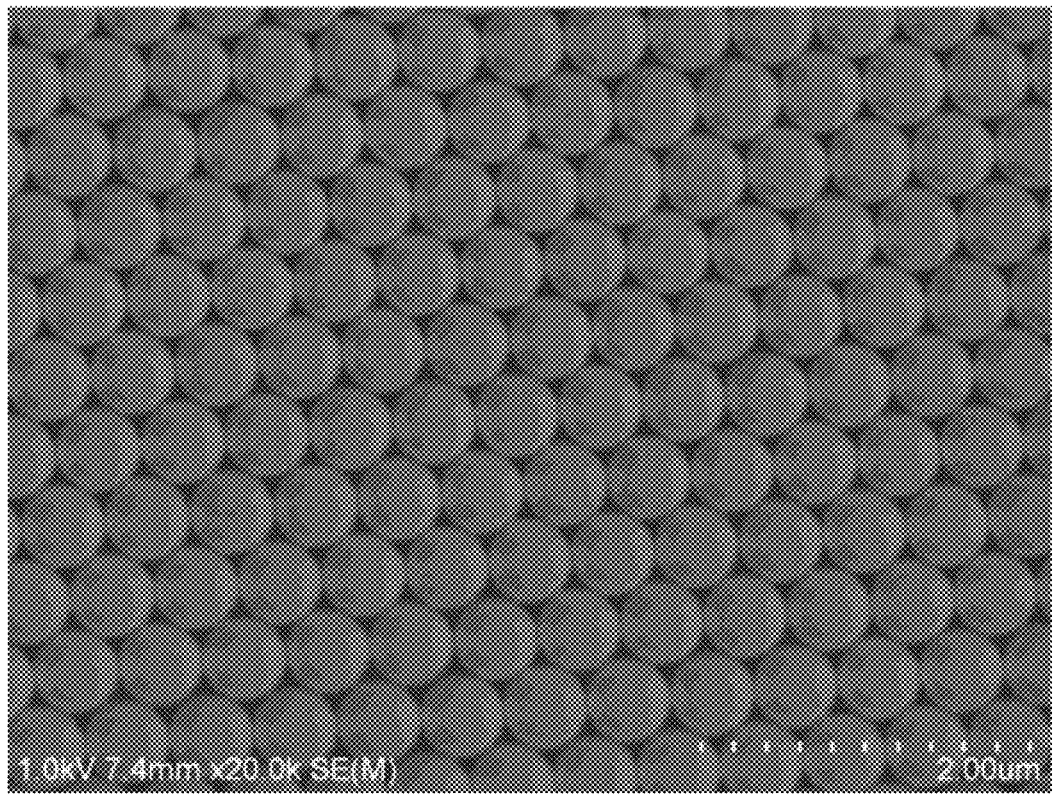
FIG. 1 is a single-layer PS small ball template.

The present invention is further illustrated hereafter in conjunction with specific embodiments to enable those skilled in the art to better understand and practice the present invention, but these embodiments are not intended to limit the present invention.

(1) Anti-Reflection Performance Test

The ultraviolet-visible reflection spectrum and the absorption spectrum of all samples were tested by a UV-3600plus ultraviolet-visible spectrophotometer of Shimadzu, Japan. The scanning speed was medium speed, and the test range was 200-1,500 nm.

(2) Micro-Morphology Test

The micro-morphology of the samples was observed by a scanning electron microscope, model S-4800, Hitachi Company, Japan. All the samples were not needed to be treated by metal spraying.

(3) Element Composition Test

The element composition and content of the samples were analyzed by an X photoelectron spectrometer cooperated with a field emission scanning electron microscope.

(4) X-Ray Diffractometer (XRD)

The crystal forms of the samples were analyzed by an XRD, model D8, Bruker AXS Co., Ltd, Germany. The test range was 20-80°.

(5) Raman Test

All the samples were subjected to Raman performance test by an in Via micro confocal Raman spectrometer, Renishaw Trading Co., Ltd, UK. Firstly, R6G was selected to be used as a probe molecule, and the concentration was $10^{-4}$ to $10^{-13}$ M. Then, 10 μL of R6G solutions with different concentrations were dripped to surfaces of SERS substrates. Finally, the above samples were subjected to Raman test.

Embodiment 1: Preparation of Bionic Compound Eye SERS Substrate of Ag Bowl/Silicon Pyramid Cone The present application designed a bionic SERS substrate of an Ag-based compound eye bowl structure, and constructed a continuous Ag nanobowl array on a surface of a three-dimensional substrate through multi-time interface assembly and transfer. A concrete preparation process was as follows:

(1) Preparation of Polystyrene (PS) Micro Balls

Polystyrene (PS) micro balls were synthesized by an emulsion polymerization method. Styrene was taken and added into a three-neck flask. A proper amount of water was added. The three-neck flask was put into a 60° water bath kettle. Mechanical stirring was performed. After stirring for 1 h, an initiator was added. The initiator was a potassium persulfate solution. The reaction was performed for 24 h, and the PS micro balls with a diameter of 500 nm were successfully prepared. The obtained solution was washed with deionized water, centrifuged and dried for subsequent use.

(2) Assembly and Preparation of PS Ball Template

Firstly, a small amount of lauryl sodium sulfate was dripped into a petri dish containing deionized water to reduce surface tension. Then, 500 nm of PS balls were dripped onto on the liquid level in the petri dish. By using a capillary force generated by meniscuses among the PS balls in a gas-liquid interface, self-assembly was further performed to form hexagonal closely packed PS colloidal ball single-layer films, and finally, the films were transferred into a surface of a silicon wafer.

(3) Preparation of Pyramid Array (Si—C)

Firstly, a silicon wafer was cut to a size of 1 cm×2 cm, and was then cleanly cleaned to remove impurities from the surface of the silicon wafer. Finally, the treated silicon wafer was put into in a KOH solution to perform an etching reaction at a temperature of 80° C. After the reaction for 20 min, a pyramid-shaped silicon cone structure (Si—C) was obtained. An average height of the pyramid cones in the prepared pyramid array was 5 μm.

(4) Preparation of Single-Layer Silver Nanobowl/Silicon (Ag—NBs/Si—C) Composite Material Firstly, a silver nitrate water solution was added into a 100-mL three-neck flask, and was stirred for 15 min. Then, a sodium citrate water solution was added. At the same time, the close two-dimensional PS colloidal balls in step (2) were transferred into the reaction solution to react under a 90° C. heating condition for 30 min. Small balls with metal Ag films attached to the lower surfaces were successfully obtained. Finally, the composite films were fished up by the cleaned pyramid array (Si—C). The PS colloidal ball template was removed by ethanol to obtain a silver nanobowl/silicon (Ag—NBs/Si—C) composite material.

Figure 2:
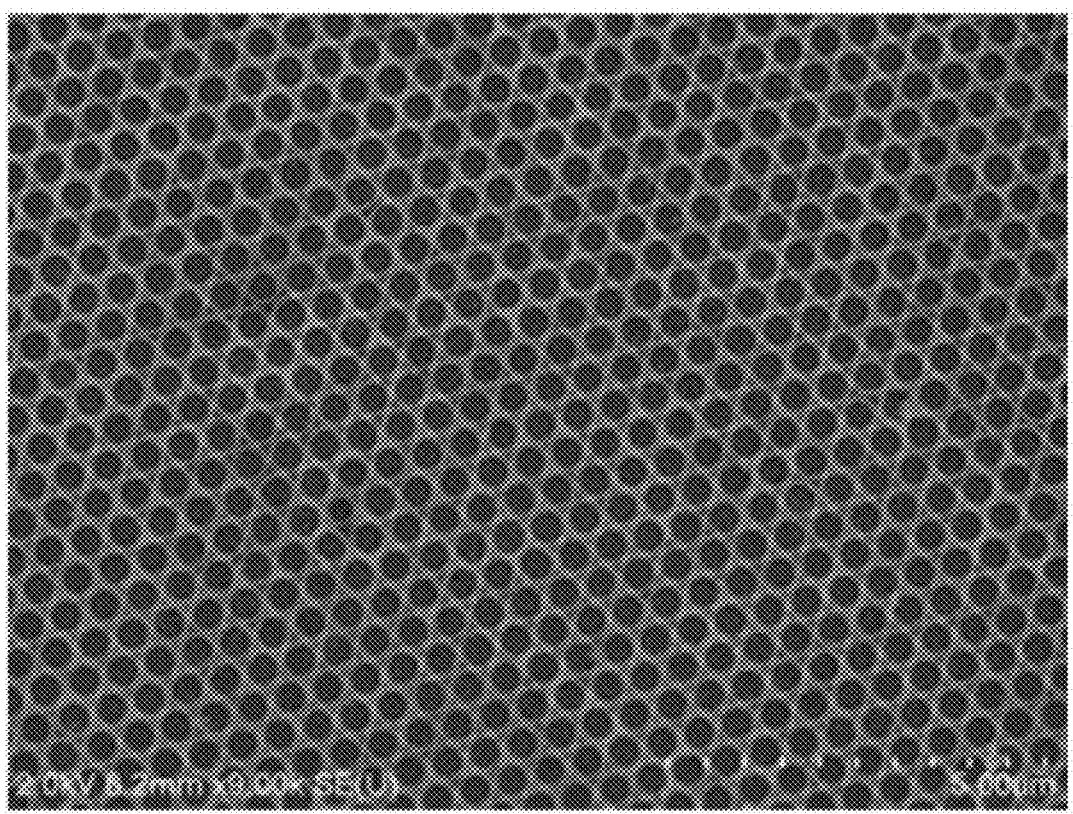
FIG. 2 is a plane silicon surface Ag nanobowl.
Figure 3:
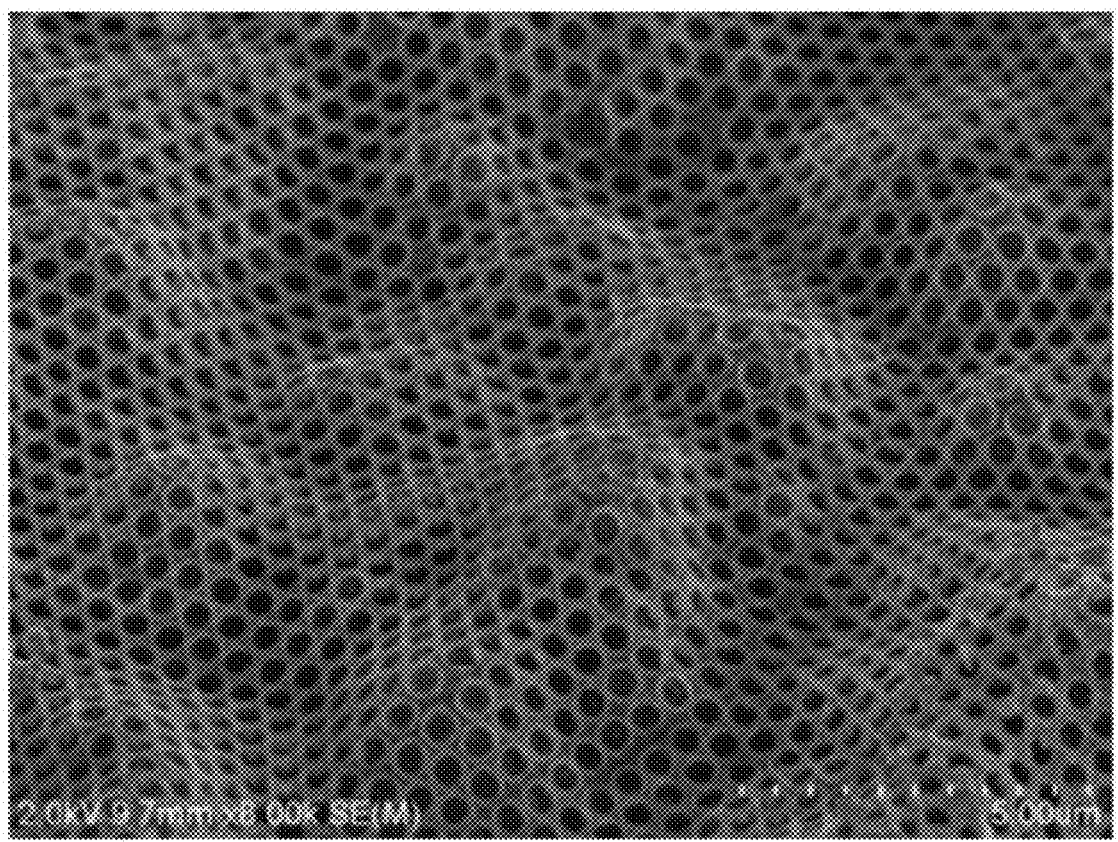
FIG. 3 is a silicon cone surface silver nanobowl.

Embodiment 2: Micro-Morphology of Bionic Compound Eye SERS Substrate of Ag Bowl/Silicon Pyramid Cone The morphologies of the small ball template, the Ag bowl and the SERS substrate involved in the process of Embodiment 1 are as shown in FIGS. 1, 2 and 3. FIG. 1 is a single-layer PS small ball template. FIG. 2 is a plane silicon surface Ag nanobowl. FIG. 3 is a silicon cone surface Ag nanobowl. In the preparation process of Ag—NBs/Si—C, when the two-dimensional PS colloidal balls were transferred into a mixed solution of silver nitrate and sodium citrate for reaction, the reaction solution was diffused to a crossing position above the high half balls of the PS ball and a tangency point plane so that the Ag nanobowls were mutually connected to form an Ag nanobowl film with good continuity. From the SEM picture, it could be seen that the Ag nanobowls and the silicon cones were completely compounded without cracks. This was because the thin Ag nanobowl film had certain toughness and could bend. The above results showed that under the induction by the PS small ball template with the diameter of 500 nm, the continuous Ag nanobowls could be formed on the surface of a plane silicon wafer, and could also be formed on the surface of the silicon cone with great fluctuation. As shown in FIG. 2 and FIG. 3, at the moment, high-regularity large-area-good 500 nm periodic hexagon structures of the original small ball template of Ag—NBs remained, round units had through hole reticular structures, there were small pores at upper sections of adjacent Ag bowls, and all of those provided more "hot spots" for SERS enhancement.

Figure 4:
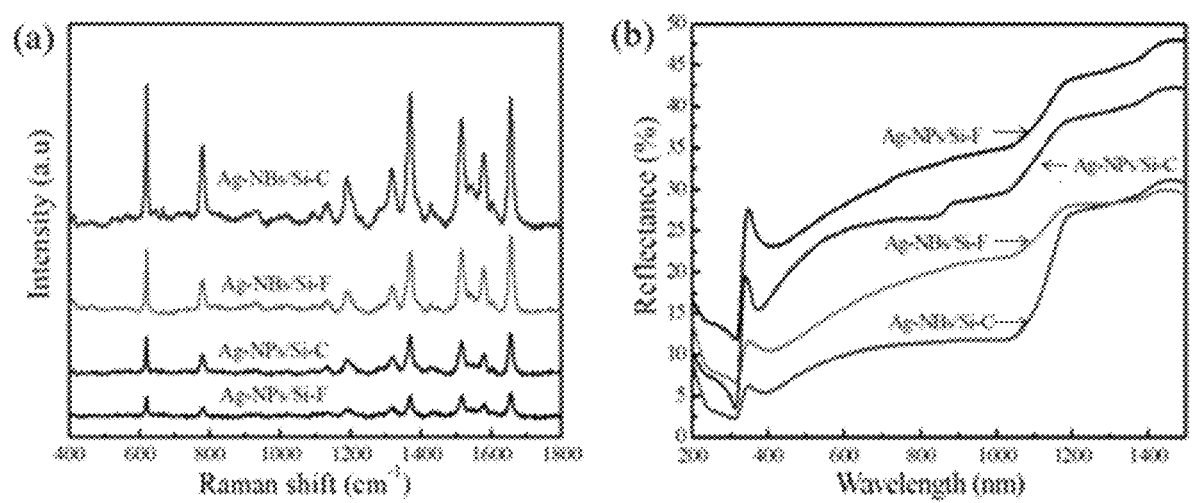
FIG. 4 is a Raman spectrum and a reflectance spectrum of different substrates (Ag—NPs/Si—F, Ag—NPs/Si—C, Ag—NBs/Si—F and Ag—NBs/Si—C): (a) Raman spectrum, and (b) reflectance spectrum.

Embodiment 3: Raman Signal of Bionic Compound Eye SERS Substrate of Ag Bowl/Silicon Pyramid Cone In order to prove that the Ag—NBs/Si—C substrate in Embodiment 1 has the advantage of improving an SERS signal, the Ag—NBs/Si—C substrate was subjected to R6G SERS signal comparison with substrates with different surface morphologies (Ag—NPs/Si—F, Ag—NPs/Si—C and Ag—NBs/Si—F), as shown in FIG. 4(a). It could be obviously seen that the Raman signal of the Ag—NBs/Si-C substrate with high light absorption capability was respectively almost 2 times, 5 times and 7 times that of Ag—NPs/Si—F, Ag—NPs/Si—C and Ag—NBs/Si—F, and the obvious enhancement was achieved on the SERS signal. The reasons were as follows: (1) Ag—NBs/Si—C had a micro-nano composite structure similar to compound eyes of mosquitoes, according to an effective medium theory, the structure was favorable for increasing the absorption on incident laser, so that the reflectivity of Ag—NBs/Si—C was lower than that of Ag—NPs/Si—F, Ag—NPs/Si—C and Ag—NBs/Si—F, as shown in FIG. 4. Therefore, Ag—NBs/Si—C could increase the absorption on Raman excitation light and could further increase the intensity of the Raman signal. (2) It is well known that the nanobowl array could greatly enhance the electromagnetic field intensity of the surface, and had more "hot spots", therefore, the SERS signals of Ag—NBs/Si—C and Ag—NBs/Si—F are stronger than those of Ag—NPs/Si—C and Ag—NPs/Si—F. (3) The Ag—NBs/Si—C substrate had stronger surface plasma resonance absorption peaks than those of Ag—NPs/Si—F, Ag—NPs/Si—C, and Ag—NBs/Si—F substrates, as shown in FIG. 4(b). The stronger plasma resonance absorption peaks were favorable for SERS signal enhancement. At the same time, Ag—NBs/Si—C had excellent sensitivity and repeatability on R6G SERS signals.

Embodiment 4: Sensing Detection of Bionic Compound Eye SERS Substrate of Ag Bowl/Silicon Pyramid Cone on $Hg^{2+}$ The SERS substrate obtained in Embodiment 1 was applied to sensing detection of $Hg^{2+}$ in water. Firstly, $10^{-4}$ M $Zn^{2+}$, $Ca^{2+}$, $Mg^{2+}$, $Mn^{2+}$, $Cr^{3+}$, $Pb^{2+}$, $Fe^{2+}$ and $Hg^{2+}$ and a mixed water solution of these ions were prepared. Then, SERS substrates with surface modified 2-mercaptoimidazole were respectively soaked into the above prepared ion solutions. Finally, the SERS substrates were taken out and were subjected to Raman spectrum analysis. Through test results, it was discovered that the Raman of the solution containing $Hg^{2+}$ could be obviously changed, and an excellent linear relationship was realized. This showed that this SERS substrate had very excellent sensing performance on $Hg^{2+}$.

Embodiment 5: Preparation of Bionic Compound Eye SERS Substrate of Au Bowl/$TiO_2$ Pyramid Cone (1) Preparation of Pyramid Silicon Cone Array Firstly, a silicon wafer was cut to a size of 1 cm×2 cm, and was then cleanly cleaned to remove impurities from the surface of the silicon wafer. Then, the clean silicon wafer was subjected to clear water modification. Finally, the treated silicon wafer was put into in a KOH solution, to perform an etching reaction at a temperature of 80° C. After the reaction for 20 min, a pyramid-shaped silicon cone structure was obtained.

(2) Preparation of PDMS Soft Template

The etched sample (1 cm×2 cm) with a pyramid structure was cleaned. Then, the silicon wafer with a silicon cone structure was covered by uniformly stirred PDMS prepolymers. Curing was performed for 3 h in a baking oven. After cooling, the PDMS was separated from the silicon wafer to obtain a recessed pyramid-shaped structure template.

(3) Preparation of $TiO_2$ Pyramid Cone-Shaped Structure

Firstly, 60 μL of $TiO_2$ sol was dripped on the substrate, and a cone surface of the PDMS template was immediately spread on the surface of the substrate attached to $TiO_2$. Then, still standing was performed for 24 h in a 180° C. environment. The PDMS template was separated from the substrate to obtain a pyramid-shaped $TiO_2$ structure. Finally, the substrate with the $TiO_2$ structure was calcined for 3 h in a tubular muffle furnace at 450° C. reached through temperature rise at a temperature rise speed of 1° C./min. An anatase type $TiO_2$ pyramid-shaped structure with a high crystallinity degree was obtained.

(4) Assembly and Preparation of Polymethyl Methacrylate (PMMA) Micro Ball Template Firstly, through self-assembly of 1570 nm PMMA micro balls through a capillary force generated by meniscuses among small balls at a gas-liquid interface, the disordered PMMA balls were closely arranged together to form a single-layer PMMA micro ball array. Then, the PMMA micro balls were transferred onto a plane carrier to further obtain a close two-dimensional PMMA colloidal ball template.

(5) Composite Au Bowl Array on $TiO_2$ Cone-Shaped Structure

Firstly, 5 mM chloroauric acid solution was prepared. 100 mL of the chloroauric acid solution was taken and added into a three-neck flask. Stirring was performed for 15 min. Then, 3 mL of a sodium citrate solution was added. At the same time, the close two-dimensional PMMA colloidal balls in step (4) were transferred into a reaction solution. Additionally, reaction was performed for 15 min under the 95° C. heating condition. Small balls with partially attached metal Au films were successfully obtained. Finally, the small balls with the metal Au films attached to the lower surfaces were fished out by the $TiO_2$ pyramid cone substrate obtained in step (3). Further, the PMMA colloidal ball template was removed to obtain a bionic compound eye SERS substrate of the $TiO_2$ pyramid cones with closely arranged Au bowls on the surfaces.

Embodiment 6: Photocatalysis Capability and Reusability of Bionic Compound Eye SERS Substrate of Au Bowl/$TiO_2$ Pyramid Cone The photocatalysis capability of the SERS substrate obtained in Embodiment 5 was tested. The photocatalysis performance of a sample was tested by a TU-1901 dual-beam spectrophotometer, Beijing Purkinje General Instrument Co., Ltd. A $10^{-5}$ M Rhodamine 6G (Rh6G) probe molecule was used as a photodegradation study object. Simulated sun irradiation was used as a catalysis light source environment. A test wavelength range was 200-800 nm. Through study, it was discovered that after light illumination for 2 h, the Rhodamine 6G (Rh6G) probe molecule on the surface of the SERS substrate was completely degraded, and the corresponding Raman signal completely disappeared. Therefore, it could be shown that this SERS substrate could be efficiently and repeatedly used.

Embodiment 7: Application of Bionic Compound Eye SERS Substrate of Au Bowl/$TiO_2$ Pyramid Cone to Detection on Pathogenic Bacteria in Food Preparation of culture medium: A nutrient broth culture medium was weighed, pH was regulated to 7.2+/−0.2, and sterilization was performed for use.

Preparation of bacterium solution: Preserved strains of pathogenic bacteria of *Escherichia coli* and *Shigella Castellani* were respectively and fast thawed, and a culture medium were inoculated with the strains by an inoculation ring to be cultured at 37° C. for 1-6 h and 100 r/min. 1 mL of the bacterium solution was taken and added into a centrifuge tube. Centrifugation was performed to remove liquid supernatant. Then, 1 mL of a sterile normal saline solution was added. After suspension, centrifugation washing was performed again to obtain a solution to be tested.

Raman detection: The SERS substrates prepared and obtained in Embodiment 5 were respectively soaked into the solution to be tested. After soaking for 1 h, cells to be detected were adsorbed onto the surfaces of the SERS substrates. The SERS substrates were taken out and dried, and were scanned by laser of a Raman spectrometer to obtain a surface enhanced Raman spectrogram of each strain. Characteristic peaks of each strain were analyzed.

Detection of unknown food sample: A solid food sample was weighed. Normal saline was added for homogenization. 1 mL of the sample was sucked and 5 to 10 mL of the liquid culture medium was inoculated with the sample for culture at 37° C. and 100 r/min. After the bacterium solution became turbid, 1 mL of the bacterium solution was sucked and added into a centrifuge tube. Centrifugation was performed to remove liquid supernatant. Then, 1 mL of a sterile normal saline solution was added. After suspension, centrifugation washing was performed again to obtain a solution to be tested. Raman detection was performed according to the above method to obtain the Raman spectrogram of the solution to be tested. The Raman spectrograms of the two kinds of pathogenic bacteria were compared and analyzed to judge whether the pollution belongs to the pollution of these two kinds of pathogenic bacteria.

Embodiment 8: Preparation of Bionic Compound Eye SERS Substrate of Cu Bowl/CdS Pyramid Cone (1) Preparation of CdS Pyramid Cone Array Firstly, a silicon substrate with a pyramid structure sequentially entered into nitric acid, sodium hydroxide and deionized water for 15 min separately, and ultrasonic concussion was performed in a cooperated way. Then, 30 mL of a $Cd(Ac)_2$ solution with a concentration of 0.008 mol/L was prepared. 20 mL of $NH_3H_2O$ was added. At the same time, 150 mL of an $SC(NH_2)_2$ solution with a concentration of 0.03 mol/L was prepared. On the basis, the solutions were mixed. Additionally, the silicon substrate with the pyramid structure subjected to surface treatment was fast immersed into the mixed solution. Reaction was performed for 60 min under the condition of 90° C. Finally, CdS pyramid cones were obtained.

(2) Assembly of Silicon Dioxide ($SiO_2$) Micro Ball Template

Firstly, self-assembly was performed by using the capillary force of 1050 nm $SiO_2$ micro balls generated by meniscuses among the small balls at a gas-liquid interface, and disordered $SiO_2$ balls were closely arranged together to form a single-layer $SiO_2$ micro ball array. Then, the $SiO_2$ micro balls were transferred onto a plane carrier so as to obtain a close two-dimensional $SiO_2$ colloidal ball template.

(3) Compounding of Cu Bowl Array on CdS Cone-Shaped Structure

Firstly, 10 mL of a PVP water solution was added into a 500-mL three-neck flask, and was heated to 60° C. Then, 10 mL of a copper sulfate water solution with a concentration of 2.5 mol/L and the same volume of hydrazine hydrate were slowly dripped into the PVP solution at the same time. The temperature of the system was kept unchanged until the solution became dark red. Then, the close two-dimensional $SiO_2$ colloidal balls in step (2) were transferred into the reaction solution. The temperature was raised to 80° C., and the reaction time was 1 h. Small balls with partially attached metal Cu films were successfully obtained. Finally, the small balls with the metal Cu films attached to the lower surfaces were fished up by the CdS pyramid cone-shaped substrate obtained in step (1). Then, the $SiO_2$ colloidal ball template was removed to obtain the bionic compound eye SERS substrate of the CdS pyramid cone with the closely arranged Cu bowls attached to the surface.

Embodiment 9: Application of Bionic Compound Eye SERS Substrate of Cu Bowl/CdS Pyramid Cone to Detection on 2,4-dichlorphenoxyacetic Acid Residue in Fruits and Vegetables 0.1, 0.5, 1, 5 and 10 μg/mL of 2,4-dichlorphenoxyacetic acid methanol water solutions were respectively prepared. The SERS substrate prepared in Embodiment 8 was respectively soaked in the solutions. After soaking for 1 h, molecules to be detected were adsorbed onto the surface of the SERS substrate. The SERS substrate was taken out and dried, and was scanned by laser of a Raman spectrometer to obtain a surface enhanced Raman spectrogram of the solution at each concentration gradient. Characteristic peaks of the 2,4-dichlorphenoxyacetic acid were analyzed, and a standard curve of the Raman signal intensity and the corresponding 2,4-D concentration was further built.

5 g of a vegetable sample was accurately weighed. After sufficient crushing, the vegetable sample was put into a centrifuge tube. 10 mL of a 0.01 mol/L NaOH solution was added.

Concussion extraction was performed for 10 min. Then, centrifugation was performed for 5 min at 8,000 r/min. Liquid supernatant was taken. Then, the NaOH solution was added. Concussion extraction was performed for 10 min. The above operation was repeated. Extraction solutions were merged. The pH was regulated to 3.0 by 1 mol/L hydrochloric acid. After film filtration, all of the extraction solutions passed through an activated solid-phase extraction small column at a flow rate of 3 mL/min. After sample loading, 5 mL of hydrochloric acid was used for rinsing. After rinsing, on a solid-phase extraction device, vacuum moisture extraction was performed to an almost dry state. Then, elution was performed by 1 mL of methanol, and was repeated for 4 times. Eluants were merged. Nitrogen gas was used for blowing to an almost dry state. The volume was regulated to 5 mL by a methanol water solution. The SERS substrate prepared and obtained in Embodiment 8 was soaked in the above solution. After soaking for 1 h, molecules to be detected were adsorbed onto the surface of the SERS substrate. The SERS substrate was taken out and dried, and was scanned by laser of a Raman spectrometer to obtain a surface enhanced Raman spectrogram. In combination with a standard curve, the content of 2,4-dichlorphenoxyacetic acid in the sample was obtained and was 0.85 μg/g.

The above-mentioned embodiments are merely exemplary embodiments for fully illustrating the present invention, and the protection scope of the present invention is not limited thereto. The equivalent substitution or change made by those skilled in the art on the basis of the present invention all falls within the protection scope of the present invention. The protection scope of the present invention is defined by the claims appended hereto.

What is claimed is:

1. A construction method of a bionic SERS substrate of a metal-based compound eye bowl structure, comprising the following steps:
   (1) performing self-assembly on small balls with a diameter of 0.01-10 μm in a gas-liquid interface to obtain closely arranged single-layer balls;
   (2) transferring the single-layer balls obtained in step (1) to a gas-liquid interface of a precursor reaction solution required for preparing a metal bowl to grow metal films on surfaces of the small balls below the liquid level in situ, so as to obtain the small balls with the metal films attached to the lower surfaces; and
   (3) transferring the small balls with the metal films attached to the lower surfaces obtained in step (2) to a surface of the cone-shaped structure substrate, and then removing the small balls to obtain the bionic SERS substrate of the metal-based compound eye bowl structure that comprises the cone-shaped structure substrate and metal bowls coating the surface of the cone-shaped structure substrate, wherein the metal bowls are of a continuously and closely arranged single-layer bowl structures, and the metal bowl has a height of 0.01-10 μm and a bowl opening diameter of 0.01-10 μm; and the cone-shaped structure substrate is a micron pyramid cone, and the micron pyramid cone has a height of 1-100 μm.

2. The method according to claim 1, wherein the precursor reaction solution required for preparing the metal bowl is a reaction solution containing one or more elements of gold, silver, palladium, platinum, copper, lithium or sodium.

3. The method according to claim 1, wherein a material of the small balls is one of silicon dioxide, polystyrene, polymethyl methacrylate, polyacrylic acid, polylactic acid, chitosan, gelatin, albumin, starch or a derivative of these materials.

4. The method according to claim 1, wherein in step (3), during transferring, the cone-shaped structure substrate is used for directly supporting the small balls with the metal films attached to the lower surfaces from a solution.

* * * * *